(12) United States Patent
Kaster, Jr. et al.

(10) Patent No.: US 6,750,377 B1
(45) Date of Patent: Jun. 15, 2004

(54) METHOD OF BREEDING GLYPHOSATE RESISTANT PLANTS

(75) Inventors: Larry V. Kaster, Jr., Ames, IA (US); Tzao Fen Huang, Ames, IA (US); James J. Reysack, Ankeny, IA (US); Alan F. Hawkins, Ankeny, IA (US)

(73) Assignee: Advanta Technology Ltd., Sleaford (GB)

( * ) Notice: Subject to any disclaimer, the term of this patent is extended or adjusted under 35 U.S.C. 154(b) by 0 days.

(21) Appl. No.: 09/100,516

(22) Filed: Jun. 19, 1998

(51) Int. Cl.[7] ................................................. A01H 1/04
(52) U.S. Cl. ...................... 800/266; 800/271; 800/272; 800/275
(58) Field of Search .............................. 800/300, 300.1, 800/301, 288, 271, 274, 275, 266, 272

(56) References Cited

U.S. PATENT DOCUMENTS

| | | | |
|---|---|---|---|
| 4,443,971 A | | 4/1984 | Chaleff |
| 4,517,763 A | | 5/1985 | Beversdorf et al. |
| 4,658,084 A | | 4/1987 | Beversdorf et al. |
| 4,735,649 A | * | 4/1988 | Dhingra et al. ................ 71/86 |
| 5,331,107 A | | 7/1994 | Anderson et al. |
| 5,777,196 A | * | 7/1998 | Hall ............................ 800/200 |
| 6,040,497 A | * | 3/2000 | Spencer ....................... 800/288 |
| 6,057,496 A | | 5/2000 | Conner |

OTHER PUBLICATIONS

Siminsky et al. Expression of a soybean cytochrome P450 monooxygenase cDNA in yeast and tobacco enhances the metabolism of phenylurea herbicides. Proc. Natl. Acad. Sci. USA Feb. 1999 vol. 96, pp. 1750–1755.*

E. Frascaroli et al., Haplo–diploid gene expression and pollen selection for tolerance to acetochlor in maize, Theor Appl Genet (1994) 88:780–784.

M.S. Gorla et al., Herbicide–tolerant corn by pollen selection, Sex Plant Reprod (1989), 2:65–69.

E. Frascaroli et al., Variability of pollen and plant responses to glyphosate in maiz, J. Genet & Breed (1992) 46:49–56.

* cited by examiner

Primary Examiner—Amy J. Nelson
Assistant Examiner—David H Kruse
(74) Attorney, Agent, or Firm—Dana S. Rewaldt

(57) ABSTRACT

The invention relates to a method of breeding plants that are glyphosate resistant due to a transgene whereby all of the resulting progeny plants or seed are also glyphosate resistant due to inheritance of the transgene by elimination of male gametes that do not carry a resistance transgene.

11 Claims, No Drawings

METHOD OF BREEDING GLYPHOSATE
RESISTANT PLANTS

FIELD OF THE INVENTION

The present invention relates to a method of producing herbicide resistant plants. This method is useful in the production of hybrids as well as in the production of transgenic plants generally.

BACKGROUND OF THE INVENTION

Incorporation of a gene which confers resistance to the herbicides such as glyphosate into plants is well known (see. for example Gasser et al., Recent Adv—Phytochem, New York, Plenum Press 1988 22, p45–59). Such plants, in particular corn plants, are available on the market, for example from DeKalb Genetics. In the case of glyphosate resistance, the plants include a gene which brings about a glyphosate-resistant, GA21, which is based on the gene encoding an altered an altered active site enzyme.

For example diploid plants may be homozygous (termed RR where R is glyphosate resistance) or heterozygous Rr for glyphosate resistance, depending upon their method of production and lineage.

When used in plant breeding programmes, heterozygous plants will result in the production of a significant proportion of plants which do not possess the herbicide resistance trait. For example, when dealing with glyphosate resistant plants, this may be represented diagrammatically by:

$Rr*Rr>RR+2Rr+rr$

R=the transgene and r=azygous wildtype

Where one of the parents does not carry the resistance trait, even more of the progeny will lack the trait i.e.

$rr*Rr>rR+rr$

This means that heterozygous plants cannot normally be used as gene donors in the production of commercial seed for farmers togrow, because much of the seed would lack the trait, and desired levels of purity would not be achieved.

However, the use of heterozygous plants could actually be preferred to the use of homozygotes in seed production. This is because the phenomenon of gene silencing, in which transformation events become unstable or stop functioning after several generations, occurs more frequently in homozygous plants.

There is a need for a process whereby the yield of plants demonstrating a desired trait, such as herbicide resistance, is increased from breeding programmes which include heterozygous plants.

SUMMARY OF THE INVENTION

The applicants have found that by applying a herbicide at a particular stage of plant development, maintenance of the herbicide resistance in the pollen and therefore in the progeny can be enhanced.

The invention provides a method of producing a plant which shows resistance to a herbicide, said method comprising
(i) applying said herbicide to a population of herbicide resistant plants at an advanced vegetative stage before flowering,
(ii) using pollen from said plants to fertilise female plants; and
(iii) obtaining progeny therefrom.

The method of the invention may be applied to plants which are resistant to various herbicides. In particular it may be applied to non-selective herbicides in which the method of plant resistance to the herbicide is achieved through a modified endogenous gene which produces a plant that is unaffected by the presence of the herbicide.

A particular herbicide for use in the method of the invention is glyphosate and salts thereof such as those sold as Roundup™ and Touchdown™. Other herbicides which may be used in this way are Acetolactate Synthase (ALS) and (AHAS)inhibitors (sold as Pursuit™ and Sceptre™), where the herbicide resistant mechanism of the plant is alteration of the active site as described above.

The invention is particularly applicable where the plants are crop plants such as grasses particularly corn.

What constitutes a suitable "advanced vegetative stage" may vary from plant to plant, depending upon the pollen development. This may be determined in each case using routine test methods. However in general, it will comprise a stage equivalent to V5 or above, for example up to V16 in corn. A description of these growth stages in corn is given by S. W. Ritchie et al., "How a Corn Plant Develops. Rev. Feb. 1982" Special Report (Iowa State University of Science and Technology, Cooperative Extension Service, No. 48) 1982, 21 p: col.ill;, the content of which is incorporated herein by reference.

The invention is based upon the statistically significant deviance of observed segregation from expected segregation that observed in series of experiments. The glyphosate resistance allele, designated as R, behaves in a dominant fashion. Therefore, plants either homozygous R (i.e. RR) or heterozygous R (i.e. Rr) will be resistant to foliar applications of glyphosate. Starting from a known allelic composition, the observed segregation can be statistically compared with the expected segregation by using a Chi-Square test, a readily accepted statistical tool for comparing the deviation of observed from expected values. It was found that, using this method of analysis, the segregation varied in a statistically significant manner.

Specifically, it has been observed that a corn plant which is heterozygous for the Glyphosate-resistance event GA21 behaves as if it were RR when used as a pollen parent in a cross to another corn plant Specifically, it has been observed that a corn plant which is heterozygous for the Glyphosate-resistance event GA21 behaves as if it were RR when used as a pollen parent in a cross to another corn plant and when it has first been sprayed with glyphosate at a relatively advanced vegetative stage, but before flowering. Conversely, if the Rr plant is not sprayed with glyphosate, or if the spray is delivered at an early vegetative growth stage, the plant behaves normally, and contributes both R and r pollen to the cross.

Diagrammatically:

With glyphosate $rr*Rr>Rr$ only

Without glyphosate, or glyphosate early $rr*Rr>rR+rr$

Similar effects are not seen with female gametes, or seed set.

Without being limited by any theory or mode of actions, it is thought that residual herbicide within the plant kills, or inactivates, r pollen during development. This is consistent with the known mode of action of the herbicide glyphosate, which is translocated readily in the plant and which will accumulate at sites of high metabolic activity (sinks) such as the developing tassel and anthers. It is noteworthy also that GA21 is an alternative-enzyme method of protection, not a herbicide degradation system, so GA21 itself should not affect the distribution and persistence of the herbicide in the plant.

The method of the invention can be used in several ways. In one way, it may be used to improve the purity of inbred and hybrid seed production (especially herbicides resistant crops, by preventing the production of pollen lacking the desired genes.

Normal standards for seed production allow 2–4% offtypes in hybrid seed. However, if the crop contains a herbicide resistance trait, and the trait is not present in the offtypes, these will be killed when the farmer uses the herbicide for weed control. Death of these plants can cause farmer concern and, theoretically at least, could somewhat reduce yield (to the extent that the offtypes, had they survived, would have set grain). This has become a significant issue in the USA during the last couple of years.

One possible source of offtypes occurs when the male parent is used as the trait donor in a production field, and (using glyphosate as an example) contains either rr or Rr genotypes as well as the desired homozygote, RR. Obviously, we can use glyphosate itself to eliminate rr from the male rows, so they are not a problem. But, because the trait is dominant, the herbicide will not eliminate the Rr plants. However, using a late vegetative spray of pollen as described above will eliminate the r pollen from these heterozygotes, so they will behave as RR. Hence, one source of susceptible offtypes will be prevented.

Thus in a further aspect, the invention provides, in the production of herbicide resistant hybrid seed, a method of reducing the numbers of herbicide susceptible offtypes in a population of herbicide resistant hybrids, said method comprising spraying male parent plants with said herbicide at late vegetative stage of growth such that any heterozygotes amongst the population will produce pollen which show herbicide; resistance as the dominant trait.

The method of the invention may also be used in the production of transgenic plants. Frequently, herbicide resistance is used as a selectable marker to allow selection of successful transformants which include a desired trait gene. In broad terms, plants are cotransformed with the desired trait gene as well as a herbicide resistance gene. The trait gene and the herbicide resistance gene are preferably linked so that both share similar fate in the transformation process. Application of herbicides to the transformants will eliminate unsuccessful transformants which are not resistant to the herbicide, leaving only those plants which include the desired trait gene.

Using the method of the invention, linkage, and preferably tight linkage, of the desired trait gene to the herbicide resistance gene will maximise the production of trait containing pollen from male plant rows, even if the rows contain heterozygotes. The advantages associated with the use of this pollen in breeding programmes are clear.

Thus in a further aspect the invention provides a method of transforming a plant with a desired transgene, said method comprising
(i) transforming plant cells with:
    (a) a construct which comprises a desired transgene;
    (b) a herbicide resistance gene;
(ii) growing plants from said cells;
(iii) applying herbicide to plants grown in step (b) at an advanced vegetative stage so as to ensure that the pollen produced from surviving plants carries herbicide resistance and the desired trait in a dominant form;
(iv) using pollen produced in step (iii) to fertilise a female parent, and
(v) obtaining the progeny thereof.

Suitably the desired transgene and the herbicide resistance gene will be on the same construct prior to the transformation, although co-transformation procedures as are known in the art, may also be used.

This method is particularly advantageous in that it delivers a desired trait at high purity from the male parent.

Desired transgenes are well known in the art. They include genes which control sterility and/or fertility as well as genes which cause quality traits such as high oil.

This effect can be used in hybridization technology in particular. For example, by using herbicide resistance such as glyphosate resistance as a selectable marker/part of the construct for a male gametophyte killer gene (male sterility gene S), plants of structure RSrs can be created. If this is sprayed with herbicide at an advanced vegetative stage as described herein, it will be totally male sterile. This is because the S gene sterilises the R pollen, and the herbicide, such as glyphosate itself disables the r pollen. Thus, this can be used as a sterile female parent in a production field, thus eliminating the need for expensive hand-detasseling Conversely, if the plant is grown in the absence of herbicide, it will still produce r pollen. Thus the supplies of the heterozygote can be increased by growing it in a normal isolated increase field without herbicide, such as glyphosate, in which case it will set a 1:1 ratio of RSrs and rsrs seed.

The unwanted rsrs types which will also be produced in this process can be readily removed in the next generation, for example by application of the herbicide In order to increase parent seed from one generation to the next, we just spray glyphosate at an early growth stage which will eliminate the susceptible plants, but will not affect fertility of the surviving heterozygotes.

If the plants are required as female parents in a production field, they would be sprayed both early and late, first to eliminate susceptible plants, and second to enforce male sterility in the survivors. In such a system, the herbicide could be regarded as acting as a "switch" for male sterility.

Hence, in a further aspect, the invention provides a method of producing plants which are reversibly male sterile, said method comprising
(i) transforming a plant with a construct which comprises a male gametophyte killer gene (S) and a herbicide resistance gene (R),
(ii) selecting a transformant which is heterozygous with respect to said genes of structure RSrs, and either
(iii) either
    (a) where male sterile plants are required, applying herbicide to plants grown from said transformants at an advanced vegetative stage so as to disable residual fertile pollen therein, or
    (b) where male fertile plants are required, growing said plants in the absence of herbicide at the advanced growth stage.

Selection at stage (ii) is suitably carried out by applying herbicide at an early growth stage, as outlined above.

In this system, it would be helpful if the male parent in the production field also carried similar herbicide resistance, to avoid problems from spray drift onto a susceptible parent line.

This process allows the maintenance/increase of parent seed in a simple increase field rather than as a crossing block, which is required for traditional male sterility systems e.g. CMS (cytoplasmic male sterility).

For some crops such as wheat, it is highly desirable to be able to interplant the male with the female, rather than have the parents in separate rows (movement of pollen from one plant to another is a problem for hybrid wheat). In order to achieve this, the female parent line suitably carries an additional, different dominant, herbicide resistance (e.g. Liberty), whilst the male only carries only one such as glyphosate resistance. Both early and late sprays of the common herbicide in particular glyphosate would be carried out as before in order to produce male sterile females and to produce pollen which included dominant glyphosate resistance. Subsequently application of the additional herbicide, such as Liberty, post flowering would kill off the male plants.

In one particular embodiment of the invention, traits like high oil, which are expressed in the grain, could be partially switched by glyphosate. For this purpose, glyphosate resistance is used as a selectable marker/part of the construct/ tightly linked to the quality trait, and the quality trait is delivered by the pollinator (which it is in the top-cross high oil system). Then, a heterozygous pollinator would either deliver pure trait pollen, or a 1:1 mixture of trait and non-trait pollen, depending on whether it was sprayed with glyphosate at the appropriate time.

A further application of the method of the invention is in the avoidance of gene silencing for transgenes.

A major problem for transformation technology is that many transformation events become unstable, have adverse side effects on the host plant, or stop functioning, several generations down the track from the primary transformant plant. This necessitates production of many events and empirical screening to find ones which are stable and useable: it is time consuming, costly, and, at present, probably the rate-limiting step to the technology.

It has been observed that problems most frequently arise when plants are created which are homozygous for the introduced trait (TT). Normally, it is necessary to have such plants in order to create a parent which will deliver the trait in hybrid production.

Using the method of the invention, the production of homozygous plants may be avoided. Using the herbicide resistance such as glyphosate resistance as a selectable marker, it is necessary only to produce and maintain a heterozygous parental line RTrt (provided this line is used as the male in a hybrid cross). As noted above, use of herbicide such as glyphosate, sprayed selectively on the male parent in the production field, will make it function as the homozygote RTRT, although the problems associated with normal homozygotes in terms of gene silencing are avoided.

Thus in yet a further aspect, the invention provides a method of producing a transgenic plant which demonstrates a desired trait, which method comprises crossing to a female plant which lacks the desired trait, with pollen obtained from a male plant which is heterozygous for said desired trait and also for a herbicide resistance, and applying herbicide to the progeny at an advanced stage of vegetative growth in order to ensure that the trait and herbicide resistance are dominant in the pollen.

In this way, the progeny from the cross will segregate Rr or rr. The rr can be removed in the next generation by application of herbicide, thus leaving just the Rr plants. After treating with herbicide in a manner that selectively kills the r gametes, those plants can then be used a males in another cross to the female lacking the trait, producing the next cycle of Rr and rr progeny.

DETAILED DESCRIPTION OF THE INVENTION

The following examples illustrate the invention.

EXAMPLE 1

Confirmation of Heterozygosity and Establishment of Glyphosate Treatment Classes Progeny of a cross between a homozygous resistant plant (RR) and a homozygous susceptible plant (rr) were planted at the Garst Research Centre near Slater, IA, and at the Hawaii Research Centre near Kunia, HI. It was expected that none of the progeny would segregate for resistance to foliar applications of glyphosate. To test this, the progeny growing at the IA test site were sprayed with glyphosate at a rate of 64 oz per acre during the V5 and V6 stages of growth (26 days after planting). At the same time and rate, several plants in a row of known susceptible plants were sprayed. All of the sprayed plots were examined for plant mortality 7 days after spraying. As expected, all of the susceptible check plants were dead and while all of the putative heterozygous resistant plants were alive (Table 1).

TABLE 1

Observed and expected frequencies among heterozygous resistant plants treated with glyphosate during Experiment 1.

| Class | Expected Segregation | Observed Segregation |
| --- | --- | --- |
| Heterozygous Resistant | All Resistant | All Resistant None Susceptible |
| Homozygous Susceptible | All Susceptible | All Susceptible None Resistant |

A second application of 32 oz per acre was applied to the heterozyous resistant plants at the V7 to V8 stage of growth (9 days later). These plants comprised the "Sprayed" class in subsequent experiments. In HI, none of the plants were sprayed with glyphosate and these plants comprised the "Unsprayed" class in subsequent experiments. At both locations, crosses were made between the heterozygous resistant plants and homozygous susceptible plants.

EXAMPLE 2

Evaluation of Progeny from Sprayed and Unsprayed Classes

Progeny of the crosses from each class were planted at the HI location. All progeny plants from each class were sprayed with glyphosate at a rate of 64 oz per acre during the V3 to V4 stages of growth. Ten days post-application, counts of resistant and susceptible plants were made for each class. The expected segregation, 1:1 resistant to susceptible, was compared to the observed segregation for each class (Table 2). Segregation among the progeny from the Unsprayed class did not differ significantly from the expected segregation (Chi-square=2.12, d.f.=1, Prob>0.1). However, segregation among the progeny from the Sprayed class differed significantly from the expected segregation (Chi-square= 669.34, d.f.=1, Prob<0.01).

TABLE 2

Observed and expected frequencies among Sprayed and Unsprayed classes during Example 2.

| Class (Total Plant Evaluated) | Expected Segregation | Observed Segregation |
| --- | --- | --- |
| Sprayed (504) | 252 Resistant: 252 Susceptible | 504 Resistant: 0 Susceptible** |
| Unsprayed (182) | 91 Resistant: 91 Susceptible | 100 Resistant: 82 Susceptible |

**Statistically different from Expected

The absence of susceptible progeny among the Sprayed class provides clear evidence that treating heterozygous resistant plants with high doses of glyphosate at V5 and later plant growth stages imposes a selection that favours the exclusive production of resistant pollen.

What is claimed is:

1. A method of producing transgenic seed or transgenic progeny plants which have resistance to glyphosate, said method comprising:
   (i) applying said glyphosate to a population of plants, at least some of said plants being heterozygous (Rr) for the glyphosate resistance transgene, said applying being at an advanced vegetative state before flowering, wherein the glyphosate effectively eliminates the viability of the male gametes which do not carry the glyphosate resistant gene (R), wherein the surviving male gametes which are capable of fertilizing female gametes carry the glyphosate resistance transgene (R); and
   (ii) producing glyphosate resistant transgenic seed or transgenic plant progeny from said seed or plant population wherein the plant progeny are homozygous (RR) or heterozygous (Rr) for the glyphosate resistance transgene.

2. The method according to claim 1 wherein the plants comprise crop plants.

3. The method according to claim 2 wherein the crop plants comprise corn.

4. The method according to claim 3 wherein in step (i), the herbicide is applied at the V5 stage of growth or later.

5. The method according to claim 3 wherein in step (i), the herbicide is applied at the V5 stage of growth or later.

6. The method according to claim 1 wherein the seed are hybrid seed.

7. The method according claim 1 wherein the plants contain a second transgene.

8. The method according to claim 7 wherein the second transgene controls fertility.

9. The method according to claim 8 wherein said second transgene controls male fertility.

10. The method according to claim 1 wherein said seed are inbred seed.

11. A method of producing transgenic hybrid progeny plants which show resistance to glyphosate, said method comprising:
    (i) applying said glyphosate to a population of progenitor plants, at least some of said progenitor plants being heterozygous (Rr) for the glyphosate resistance transgene, such herbicide application being applied at an advanced vegetative state before flowering, wherein the glyphosate effectively eliminates the viability of the male gametes which do not carry the glyphosate resistant gene (R), wherein the surviving male gametes which are capable of fertilizing female gametes carry the glyphosate resistance transgene (R), such that resultant male gametes from said plants fertilize inbred female plants which are homozygous (RR) or heterozygous (Rr) for the glyphosate resistance transgene; and
    (ii) producing glyphosate resistant transgenic hybrid seed or transgenic plant progeny from said inbred female plants wherein the seed or plant progeny are homozygous (RR) or heterozygous (Rr) for the glyphosate transgene.

* * * * *